United States Patent
Neururkar et al.

[11] Patent Number: 6,136,783
[45] Date of Patent: Oct. 24, 2000

[54] ANTIFUNGAL COMPOSITIONS

[75] Inventors: Maneesh J. Neururkar, Lansdale; Michael J. Kaufman, New Hope; William A. Hunke, Harleysville, all of Pa.

[73] Assignee: Merck & Co., Inc., Rahway, N.J.

[21] Appl. No.: 09/333,245

[22] Filed: Jun. 15, 1999

Related U.S. Application Data

[62] Division of application No. 08/827,510, Mar. 28, 1997, Pat. No. 5,952,300.
[60] Provisional application No. 60/015,638, Apr. 19, 1996.
[51] Int. Cl.$^7$ .................................................. A61K 38/00
[52] U.S. Cl. ............................................. 514/11; 924/499
[58] Field of Search ........................... 514/11; 424/465, 424/499; 530/317

[56] References Cited

U.S. PATENT DOCUMENTS

| | | |
|---|---|---|
| 5,037,644 | 8/1991 | Shaked et al. . |
| 5,120,859 | 6/1992 | Webb . |
| 5,336,756 | 8/1994 | Schwartz et al. . |
| 5,378,804 | 1/1995 | Balkovec et al. ............... 530/317 |
| 5,466,781 | 11/1995 | Dorin et al. . |
| 5,514,650 | 5/1996 | Balkovec et al. . |
| 5,552,521 | 9/1996 | Belyk et al. . |
| 5,665,760 | 9/1997 | Brown et al. . |

OTHER PUBLICATIONS

"The Merck Manual," 16th edition. Berkow, editor. (1992) (Merck & Co., Inc.: Rahway NJ), p. 159–171.
The Merck Manual, 16$^{th}$ Edition, pp. 159–171 (1992).
Remington's Pharma. Sciences, pp. 1463–1469 and 1478–1484 (1980).
Remington's Pharma. Sciences. p. 238 (1980).
The Determination of Ionization Constants, 3$^{rd}$ Edition, Chapman & Hall, p. 74 (1984), by Albert, et al.
Remington's Pharma. Sciences, 18$^{th}$ Edition, Chapter 17, pp. 241–243 (1990).

*Primary Examiner*—Irene Marx
*Attorney, Agent, or Firm*—Elliott Korsen; Mark R. Daniel

[57] ABSTRACT

The invention is a pharmaceutical composition for intravenous administration to a patient comprising a) a pharmaceutically effective amount of a compound having the formula

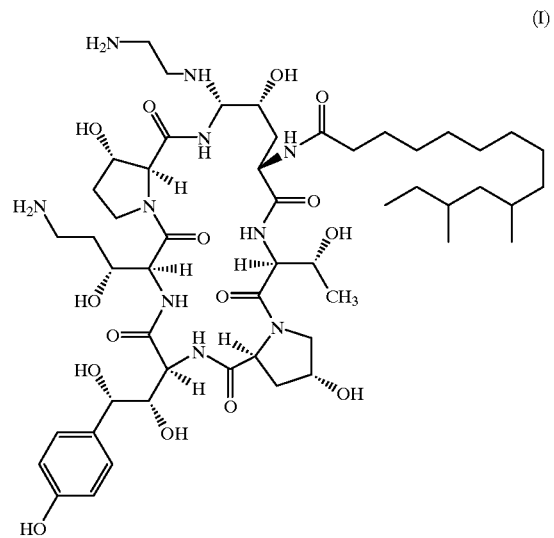

and the pharmaceutically acceptable salts thereof;

b) a pharmaceutically acceptable amount of an excipient such as a bulking agent effective to form a lyophilized cake; and c) a pharmaceutically acceptable amount of acetate buffer effective to provide a pH of between about 4 and 7.

6 Claims, No Drawings

ANTIFUNGAL COMPOSITIONS

This application is a division of Ser. No. 08/827,510 filed Mar. 28, 1997 now U.S. Pat. No. 5,952,300, and a provisional application Ser. No. 60/015,638 filed Apr. 19, 1996.

BACKGROUND OF THE INVENTION

This invention relates to compositions for treating and/or preventing fungal infections.

There is an increasing need for novel antifungal agents which are effective against opportunistic mycotic infections by such agents as Candida, Aspergillus, Cryptococcus and *Pneumocystis carinii*. The present treatments, i.e., amphotericin B and fluconazole, are inadequate due to their toxicity and resistance selection. The compositions of the present invention are considered to be both safe and fungicidal.

The compositions of the present invention contain a compound which is useful as an antibiotic, especially as an antifungal agent or as an antiprotozoal agent. As an antifungal agent, it is useful for the control of both filamentous fungi and yeast. It is especially adaptable to be employed for the treatment of mycotic infections in mammals, especially those caused by Candida species such as *C. albicans, C. tropicalis, C. krusei, C. glabrata* and *C. pseudotropicalis*, and Aspergillus species such as *A. fumnigatus, A. flavus* and *A. niger*. In particular, the compositions contain a compound which has been found effective against putatively Amphotericin B and Fluconazole-resistant Candida isolates. The compositions are also useful for the treatment and/or prevention of *Pneumocystis carinii* pneumonia to which immune compromised patients, such as those suffering from AIDS, are especially susceptible.

The compositions of the present invention are safe, stable, lyophilized dosage forms for reconstitution which are particularly useful for delivering antifungal agents to patients in need of such agents.

SUMMARY OF THE INVENTION

The invention relates to a pharmaceutical composition comprising:

a) a pharmaceutically effective amount of a compound (also referred to herein as the "active ingredient") having the formula

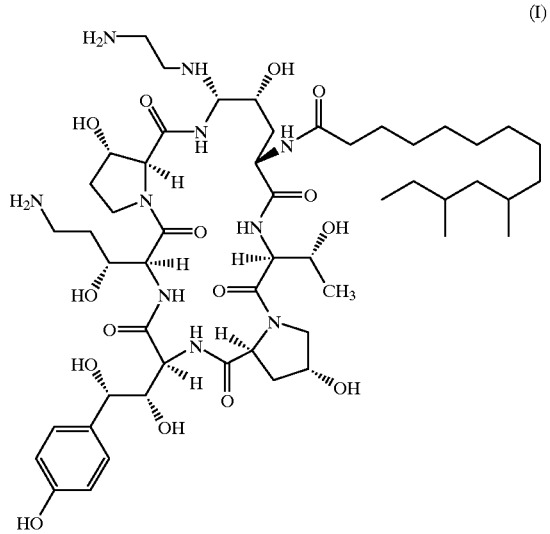

(I)

and the pharmaceutically acceptable salts thereof, b) a pharmaceutically acceptable amount of an acetate buffer effective to provide a pH of between about 4 and 7; and c) a pharmaceutically acceptable amount of an excipient such as a sucrose/mannitol mixture to form a lyophilized cake.

In a specific embodiment of this invention, the formulation is prepared as a solution of 42 mg/ml of compound I, 30 mg/ml of sucrose, 20 mg/ml of mannitol, 1.5 mg/ml (25 mM) of acetic acid, which is adjusted to about pH 6 with sodium hydroxide. The solution is subsequently filled in a vial at a volume of 1.25 ml and lyophilized. The lyophilized cake thus produced contains 52.5 mg of compound I, 62.5 mg of the sugars and 31.25 micromoles of acetate buffer per vial. The lyophilized cake is then reconstituted for use by dilution with 21 ml of a diluent. 20 ml of the diluent is withdrawn and reconstituted into a 200 ml infusion bag. The patient is then infused with this solution comprising about 0.25 mg/ml of compound I, about 0.03 millimoles or 0.15 millimolar acetate buffer, about 0.3 mg/ml of bulking agents, with the resultant composition having a pH of about 5 to 7.

DETAILED DESCRIPTION OF THE INVENTION

The formulations of the invention provide enhanced chemical stability to the pharmaceutical compositions. One advantage of such stability is extended pharmaceutical product shelf life. Prior formulations employing a tartrate buffer contained pharmaceutically significant amounts of unwanted degradation products. The use of an acetate buffered formulation results in the generation of fewer degradates and a more stable formulation. Extended pharmaceutical shelf life offers significant economic advantages.

It has been found that the compound of the formula

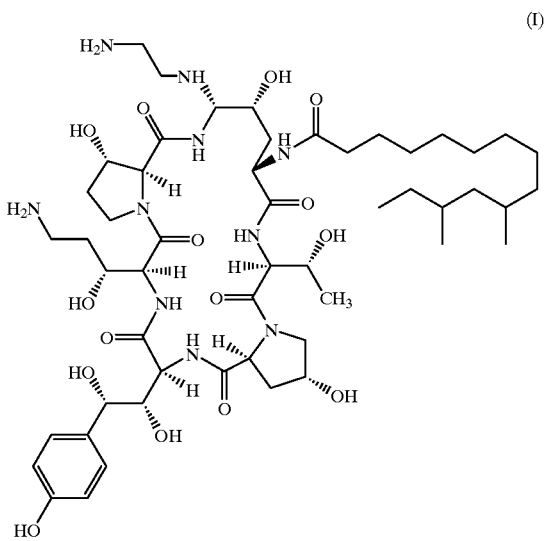

(I)

and the pharmaceutically acceptable salts thereof are significantly more stable on storage when formulated in the presence of an acetate buffer.

Compound I is claimed and described in U.S. Pat. No. 5,378,804. Methods for its preparation are disclosed in that patent as well as in U.S. Pat. No. 5,552,521 which issued on Sep. 3, 1996.

The compound by itself is highly unstable and degrades by various pathways including, but not limited to, hydrolysis, dimerization and oxidation. However, this instability was previously combated by lyophilizing the compound in a tartrate buffered formulation. This formulation, however, while relatively stable, resulted in the generation of degradates at a relatively high rate.

By switching to an acetate buffer, the lyophilized product is more stable, contains less of unwanted degradates while extending the shelf life of the composition. This makes it attractive as a commercial product.

The present invention also relates to a method for treating fungal infections caused by Candida, Aspergillus and *Pneumocystis carinii* which comprises administering the composition containing the compound of formula I to a patient in need of such treatment in an amount effective to treat the fungal infection. The invention additionally relates to a method for preventing *Pneumocystis carinii* infections in a patient which comprises administration of a preventative amount of the compound of formula I.

The acetate buffered formulation of the invention includes an amount of acetate effective to provide a pharmaceutically acceptable pH, e.g. to provide a pH environment in the range of 5 to 8, preferably about 6 to about 7. In order to provide a pharmaceutically acceptable amount of acetate buffer effective to achieve the desired pH, suitable amounts of sodium acetate and acetic acid or suitable amounts of acetic acid and sodium hydroxide can be used. The buffer is typically present in the range of about 12.5 mM to about 200 mM with a preferred range of about 25 mM to about 50 mM.

Excipients such as bulking agents, i.e., excipient sugars, are used to provide an aesthetically suitable lyophilized cake, solid dilution of the active ingredient, and sorption of available moisture. Sugars useful in the invention include sucrose, lactose, mannitol or combinations thereof. It has been found that sucrose and mannitol provide a more stable formulation and form a pharmaceutically elegant cake for the composition. The excipients are generally present in amounts of about 10–200 mg/ml with a preferred amount of about 40–60 mg/ml.

The compositions are not limited to the active ingredient, acetate buffer and bulking agent and may also include other pharmaceutically acceptable diluents, excipients or carriers. The formulations are suitable for long-term storage in glass containers commonly used in the pharmaceutical industry, e.g., in concentrated form in standard USP Type I borosilicate glass containers.

The compositions of the invention are generally prepared as follows:

1) a bulking agent or combination of agents is dissolved in water;
2) acetic acid is added and the pH is adjusted to about 3.7, if required;
3) compound I is added and dissolved with the pH subsequently adjusted to about 5 to about 6 with base;
4) the solution is filtered and filled into a lyophilization vial and frozen at −50° C.;
5) the frozen formulation is freeze dried at −20° C., with a secondary drying at 15° C. (the complete cycle takes over two days); and
6) lyophilized vials are stoppered and stored at about 5° C.

The lyophilized formulations of the compositions can be diluted at the time of administration with a suitable diluent to obtain a finished concentration, for example, of about 5.0 mg/ml, which is suitable for transfer to an infusion bag for use by the patient in need of the desired active ingredient.

The term "pharmaceutically acceptable salts" means non-toxic salts of the active ingredient, including the mono-, di- and tri-acid forms, which are generally prepared by reacting the free base with a suitable organic or inorganic acid. Pharmaceutically acceptable salts suitable as acid addition salts as well as salts providing the anion of the quaternary salt are those from acids such as hydrochloric, hydrobromic, phosphoric, sulfuric, maleic, citric, acetic, tartaric, succinic, oxalic, malic, glutamic, pamoic and the like, and include other acids related to the pharmaceutically acceptable salts listed in Journal of Pharmaceutical Science, 66, 2 (1977).

The term "pharmaceutically effective amount" shall mean that amount of active ingredient that will elicit the biological or medical response of a tissue, system or animal that is being sought by a researcher or clinician.

Compositions of the invention may be administered to patients where treatment and/or prevention of fungal infections is desired. They are useful in the treatment of Candida species such as *C. albicans, C. tropicalis, C. krusei, C. glabrata* and *C. pseudotropicalis,* and Aspergillus species such as *A. fumigatus, A. flavus* and *A. niger.* They are also useful for the treatment and/or prevention of *Pneumocystis carinii* pneumonia to which immune compromised patients, such as those suffering from AIDS, are especially susceptible.

The dosage regimen utilizing the compositions of the present invention is selected in accordance with a variety of factors including type, species, age, weight, sex and medical condition of the patient; the severity of the condition to be treated; the route of administration; the renal and hepatic function of the patient; and the particular active ingredient or salt thereof employed. An ordinarily skilled physician can readily determine and prescribe the effective amount of the drug required to prevent, counter, or arrest the progress of the condition.

Intravenously, the most preferred doses of active ingredient will range from about 1.67 to about 33 µg/kg/minute with an infusion rate of about 200 ml/hour. In order to administer this amount of active ingredient, a composition of the invention should have 0.025 to 0.50 mg/ml of active ingredient based on a 50 kg patient.

Compound I, the active ingredient, is generally prepared as follows:

Starting compound II of the formula:

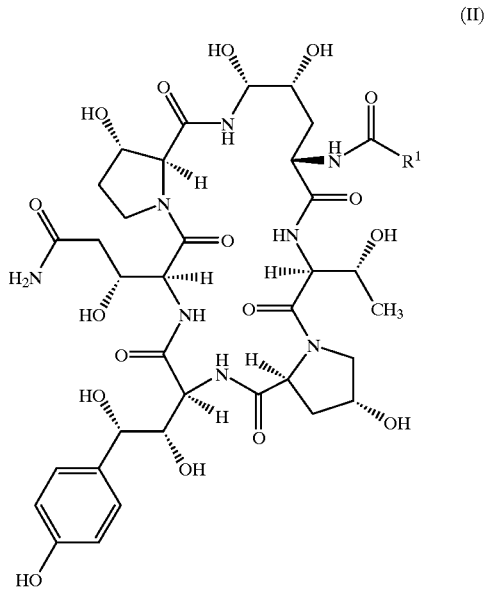

(II)

(SEQ ID No. 1)

is reduced to afford Compound III of the formula:

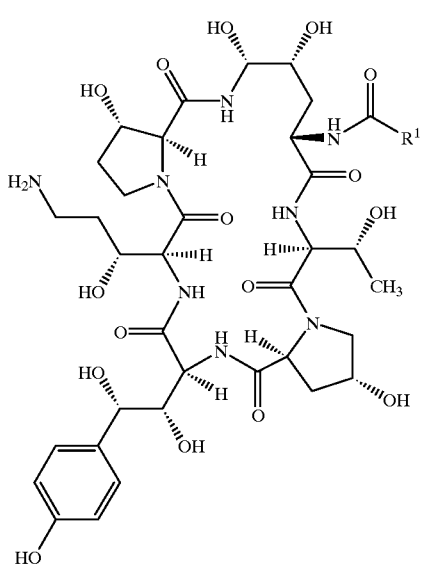

(SEQ ID No. 1)

which is subsequently converted to Compound IV of the formula:

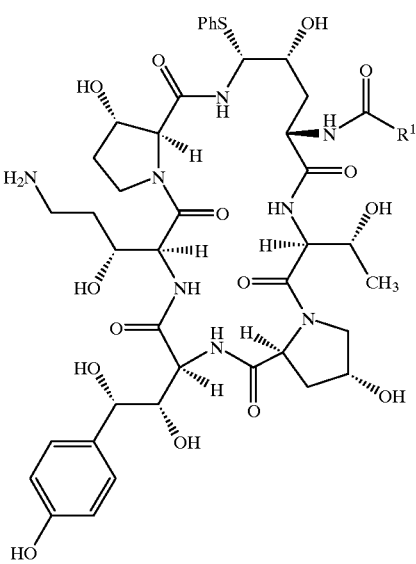

(SEQ ID No. 1)

which is stereoselectively converted to Compound I by displacement of the phenylthio group.

In an alternative process, Compound II is reacted with thiophenol to afford Compound IV-a of the formula:

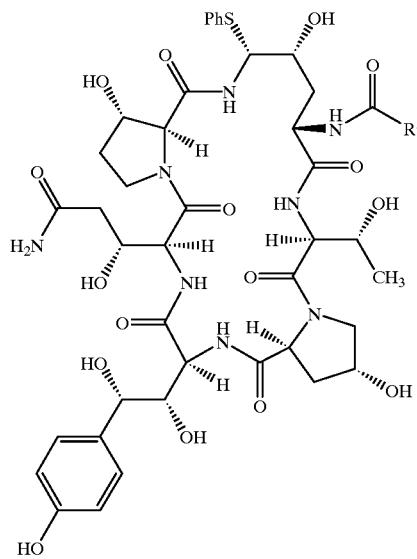

(SEQ ID No. 1)

Compound IV-a is subsequently reduced to Compound IV of the formula:

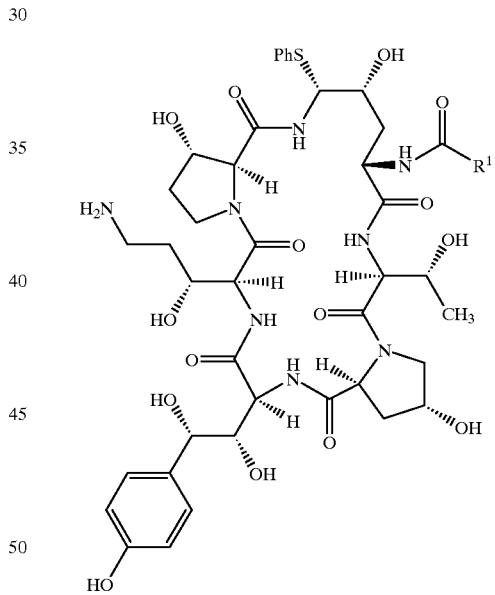

(SEQ ID No. 1)

which is stereoselectively converted to Compound I by the displacement of the phenylthio group.

PREPARATION OF COMPOUND I a) Synthesis and separation of Compound III

Compound II (15.9 g, 89 area % pure, 3.4 wt % water, 0.0128 mol) was added to dry THF (0.64 L) and the suspension was dried to <10 mol % water by refluxing through a bed of 3A molecular sieves. Additional dry THF was added to reconstitute the mixture to the original volume and the suspension was cooled to <4° C. with an ice/water/methanol bath.

Neat BH₃.SMe₂ (10.91 g, 0.144 mol) was added over ten minutes and the reaction mixture was maintained at 0–4° C. The reaction progress was monitored by HPLC until the ratio of starting material to product was 1:1 indicating the end of the reaction age (3.5 h). At 4 hours, the mixture was cooled to −12° C. and slowly quenched with 2N HCl (0.036 L). This solution was diluted to 1.14 L with water. The assay yield of Compound III was 6.60 g (47%).

The quenched solution was diluted to 4 L and loaded onto a medium-pressure column of LiChroprep RP-C18 adsorbent (158 g). After loading, the column was washed with 1.2 L water and the amine was eluted with 1.9 L of 1:4 v/v acetonitrile/water, and then 0.38 L of 1:3 v/v acetonitrile/water.

The rich cuts (>80 area %) were combined and diluted with water to a 1:7.3 v/v acetonitrile/water solution (1.70 L total). This mixture was loaded to the same column described above, and the column was washed with 0.57 L water. The desired compound was eluted with 0.57 L methanol. The rich cut fractions (>85 area %) were combined and concentrated by rotary evaporation and static high vacuum to give 6.81 g (87 wt % pure, 6.8 wt % water) containing 5.92 g of compound III (where $R^1$ is dimethyltridecyl) hydrochloride salt for an isolated yield of 43%.

b) Preparation of the phenylsulfide (Compound IV)

Compound III (5.80 g assay, 0.00533 mol) was charged to 0.23 L of dry acetonitrile and cooled to −5° C. at which point thiophenol (3.10 g, 0.028 mol) was added. TFA (36 g, 24.5 mL, 0.318 mol) was added over 20 minutes in order to keep the temperature of the reaction mixture below 0° C. The reaction was aged at −10° to 0° C. until HPLC analysis showed <3 area % starting material (3.75 h). At this time, chilled water (0.56 L) was added slowly (1 h) while cooling the reaction mixture to maintain the temperature below 5° C. The assay yield of the α- and β-phenylsulfide adduct as the trifluoroacetate salt was 4.82 g (71%).

This solution was loaded on the same column described in step a and the column was washed with water (0.57 L), then the adsorbed organic compounds were eluted with methanol (0.50 L). The rich cuts were concentrated by rotary evaporation and static high vacuum. This yielded 7.20 g (57 wt % pure, 5.1 wt % water) of crude phenylsulfide trifluroacetate salt as an amorphous foamy solid. The corrected isolated step yield for the phenylsulfide was 4.10 g (61%) as a 93:7 mixture of the α- and β-aminal diastereomers.

c) Conversion of Compound IV to Compound I-1

The crude phenylsulfide trifluoromethanesulfonate salt (8.4 g crude, 57 wt % pure, 0.00377 mole) was added to ethylenediamine (24 mL) while stirring at ambient temperature. The resulting solution was stirred 1.5 h to complete the displacement, then methanol (40 mL) was added followed by acetic acid (45 mL), keeping the temperature below 25° C. with ice-bath cooling. A thick slurry resulted. Water (160 mL) was added to dissolve the slurry, and the aqueous layer was extracted by gentle shaking with hexanes (75 mL). The hexanes layer was back-extracted with water (40 mL) and the combined aq. layer was filtered through a medium-porosity sintered glass funnel, then purified by prep HPLC using a 50 mm diameter C18 column, using 22% acetonitrile/78% 0.15% aq. acetic acid as eluent. The rich cut was lyophilized to provide 4.2 g of 85 wt % pure Compound I-1 as the diacetate salt in 78% isolated step yield.

d) Crystallization of Compound I-1

The solid (2.3 g) was dissolved in ethanol (25 mL) and water (2.7 mL) was then added. The solution was passed through a sintered glass funnel to remove extraneous matter. To this filtrate was added acetic acid (0.14 mL) followed by the slow addition (1.75 h) of ethyl acetate (14 mL). The solution was seeded and the seed bed was aged for 1 h. The remaining ethyl acetate (32 mL) was added over 5 h and aged an additional 1 h. The crystalline solid was collected on a sintered-glass funnel and washed with a solution of ethanol/ethyl acetate/water (6 mL/9 mL/0.5 mL, respectively). The wet cake was dried with a nitrogen flow to give 1.91 g (1.75 assay g, 88% recovery) of the diacetate salt of compound I-1.

EXAMPLE 1

Preparation Of Formulation 1

| Ingredient | Amount |
| --- | --- |
| Compound I | 42 mg/ml |
| sucrose | 30 mg/ml |
| mannitol | 20 mg/ml |
| acetic acid | 1.5 mg/ml |
| sodium hydroxide | q.s. to pH 5 to 6.2 | fill volume—0.875 ml to 1.8 ml

Typically, to a 25 mL volumetric flask was added 0.75 g of sucrose and 0.5 g of mannitol, about 17.5 mL of water, 0.5 mL of a 75 mg/mL acetic acid solution, and 42 mg/ml equivalent of Compound I. The solution was mixed and the pH was adjusted to 6 using 1M NaOH. The volume was adjusted with water and the pH was confirmed. The solution was filtered through a Millex-GV syringe filter and filled into 10 mL tubing glass vials at 1.75 mL each. The vials were partially stoppered with lyophilization stoppers and lyophilized to yield a solid lyophilized cake at the bottom of the vial.

The lyophilized formulation is diluted with 10.5 ml, and 10 ml is withdrawn and diluted into 200 ml resulting in a finished concentration of 0.25 mg/ml prior to administration to the patient.

Additional formulations were prepared as described above containing the following ingredients (each of the formulations was prepared at a solution concentration of 40–42 mg/ml of active ingredient):

TABLE 1

| Ex | Buffer | Sugar(s) |
| --- | --- | --- |
| 2 | Tartrate 50 mM (7.5 mg/ml) | None |
| 3 | Tartrate 50 mM (7.5 mg/ml) | Lactose (30 mg/mL) Mannitol (20 mg/mL) |
| 4 | Tartrate 50 mM (7.5 mg/ml) | Mannitol (50 mg/mL) |
| 5 | Acetate 25 mM (1.5 mg/ml) | Lactose (30 mg/mL) Mannitol (20 mg/mL) |
| 6 | Tartrate 50 mM (7.5 mg/ml) | Sucrose (50 mg/mL) |
| 7 | Acetate 25 mM (1.5 mg/ml) | Sucrose (50 mg/mL) |
| 8 | Acetate 50 mM (3.0 mg/ml) | Lactose (30 mg/mL) Mannitol (20 mg/mL) |

The formulations were stored in the lyophilized state at 5° C. and tested at about 4 week intervals for stability. Stability and formation of degradates was determined by gradient HPLC using standard methods known to one skilled in the art.

It was surprisingly found that Formulations 1, 5, 7 and 8 were significantly more stable and showed significantly less of the unwanted degradates than the other formulations.

What is claimed is:

1. A method for treating an infection caused by Candida sp. in a patient which comprises administering intravenously to said patient an effective amount of a composition comprising 42 mg/ml of a compound having the formula

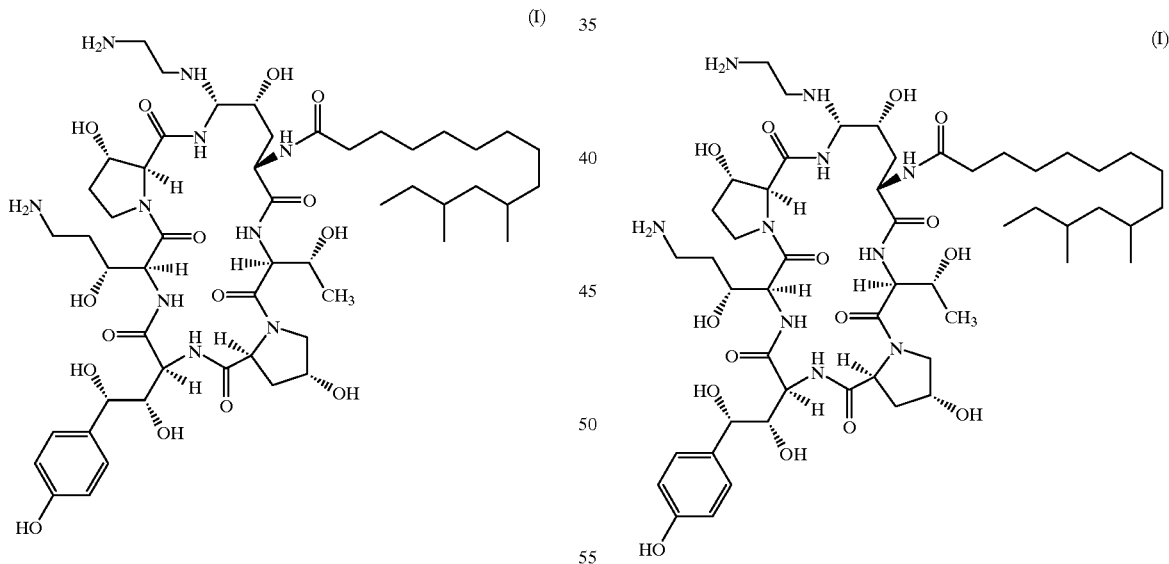

or a pharmaceutically acceptable salt thereof, 25 mM of an acetate buffer, 30 mg/ml of sucrose, 20 mg/ml of mannitol, and water.

2. A method for treating an infection caused by Candida sp. in a patient which comprises administering intravenously to said patient an effective amount of a composition comprising 42 mg/ml of a compound having the formula or a pharmaceutically acceptable salt thereof, 50 mM of an acetate buffer, 30 mg/ml of sucrose, 20 mg/ml of mannitol, and water.

3. A method for treating an infection caused by Aspergillus sp. in a patient which comprises administering intravenously to said patient an effective amount of a composition comprising 42 mg/ml of a compound having the formula

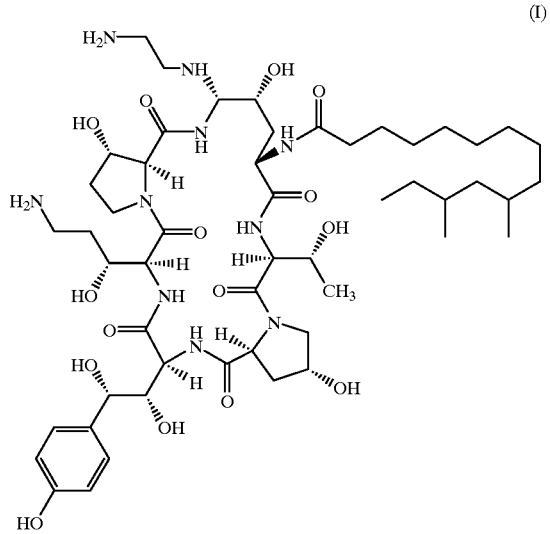

(I)

or a pharmaceutically acceptable salt thereof, 25 mM of an acetate buffer, 30 mg/ml of sucrose, 20 mg/ml of mannitol, and water.

4. A method for treating an infection caused by Aspergillus sp. in a patient which comprises administering intravenously to said patient an effective amount of a composition comprising 42 mg/ml of a compound having the formula

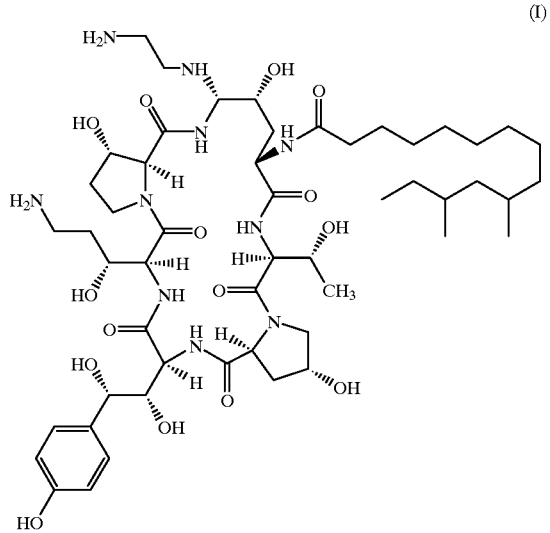

(I)

or a pharmaceutically acceptable salt thereof, 50 mM of an acetate buffer, 30 mg/ml of sucrose, 20 mg/ml of mannitol, and water.

5. A method for treating or preventing an infection or condition caused by *Pneumocystis carinii* in a patient in need of such treatment or prevention which comprises administering intravenously to said patient a preventative or therapeutic amount of a composition comprising 42 mg/ml of a compound having the formula

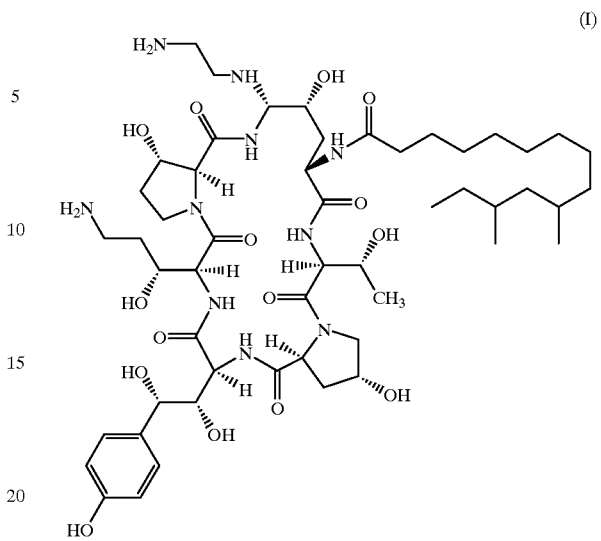

(I)

or a pharmaceutically acceptable salt thereof, 25 mM of an acetate buffer, 30 mg/ml of sucrose, 20 mg/ml of mannitol, and water.

6. A method for treating or preventing an infection or condition caused by *Pneumocystis carinii* in a patient in need of such treatment or prevention which comprises administering intravenously to said patient a preventative or therapeutic amount of a composition comprising 42 mg/ml of a compound having the formula

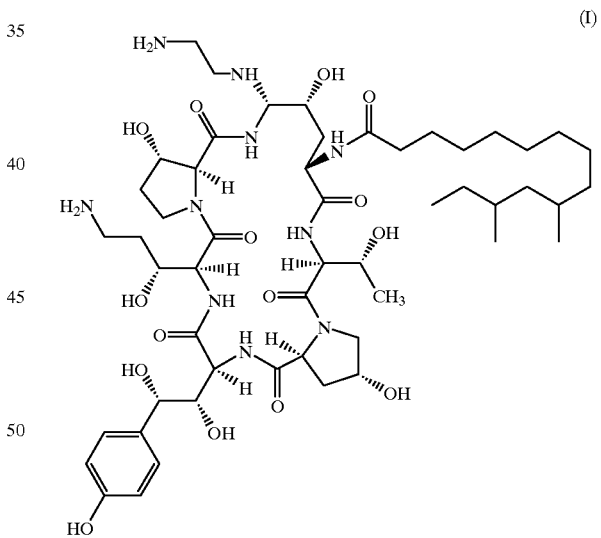

(I)

or a pharmaceutically acceptable salt thereof, 50 mM of an acetate buffer, 30 mg/ml of sucrose, 20 mg/ml of mannitol, and water.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS: unknown
      (D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:1:

```
Xaa Thr Xaa Xaa Xaa Xaa
1               5
```